United States Patent [19]

Mueller

[11] 4,075,407
[45] Feb. 21, 1978

[54] HETEROCYCLIC PHOSPHONIUM SALTS

[75] Inventor: Richard A. Mueller, Northbrook, Ill.

[73] Assignee: G. D. Searle & Co., Chicago, Ill.

[21] Appl. No.: 741,909

[22] Filed: Nov. 15, 1976

Related U.S. Application Data

[63] Continuation-in-part of Ser. No. 577,675, May 15, 1976, Pat. No. 3,997,588.

[51] Int. Cl.$^2$ ............... C07D 307/10; C07D 313/04; C07D 309/04
[52] U.S. Cl. ................... 542/412; 260/333; 260/345.1; 260/345.9 R; 260/347.8; 260/346.11; 424/203
[58] Field of Search .......... 260/345.1, 240 P, 346.1 R, 260/345.9, 347.8, 333; 424/203

[56] References Cited

U.S. PATENT DOCUMENTS

| | | | |
|---|---|---|---|
| 3,658,847 | 4/1972 | Fried | 260/240 D |
| 3,682,970 | 8/1972 | Henrick et al. | 260/327 M |
| 3,714,153 | 1/1973 | Martel et al. | 260/240 R |

OTHER PUBLICATIONS

Shaffer Dissertation Abstracts, 1967, p. 950B.

Primary Examiner—Arthur P. Demers
Attorney, Agent, or Firm—John J. McDonnell

[57] ABSTRACT

Heterocyclic phosphonium salts of the following compound

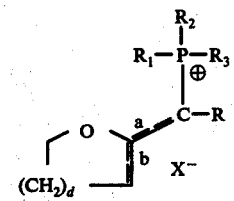

wherein $d$ is 1, 2 or 3; R is hydrogen or an alkyl containing 1-3 carbon atoms; $R_1$, $R_2$ and $R_3$ is each an alkyl radical containing 1-6 carbon atoms, a cycloalkyl radical containing 5 or 6 carbon atoms, or

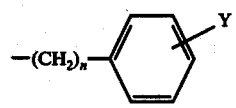

wherein $n$ is 0-4, and Y is hydrogen, halogen, alkyl containing 1-6 carbon atoms or alkoxy containing 1-6 carbon atoms; $X^-$ is a pharmacologically acceptable anion; and one of $a$ and $b$ is a double bond and the other is a single bond. The compounds display valuable pharmacological properties, and are particularly useful as analgesic agents.

20 Claims, No Drawings

HETEROCYCLIC PHOSPHONIUM SALTS

This is a continuation-in-part of application Ser. No. 577,675, filed May 15, 1976, now U.S. Pat. No. 3,997,588.

SUMMARY OF INVENTION

The present invention relates to a group of compounds which are heterocyclic phosphonium salts and, in particular, to compounds of the following formulas

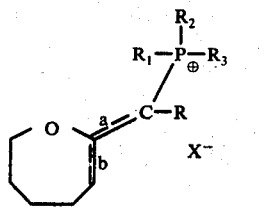

wherein R is hydrogen or an alkyl containing 1-3 carbon atoms; $R_1$, $R_2$ and $R_3$ is each an alkyl radical containing 1-6 carbon atoms, a cycloalkyl radical containing 5 or 6 carbon atoms, or a radical of the formula

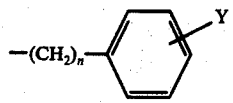

wherein n is 0-4, and Y is hydrogen, halogen, alkyl containing 1-6 carbon atoms or alkoxy containing 1-6 carbon atoms; $X^-$ is a pharmacologically acceptable anion; and one of a and b is a double bond and the other is a single bond;

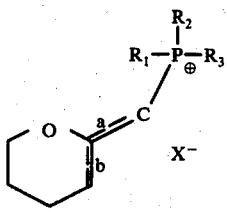

wherein R, $R_1$, $R_2$, $R_3$, $X^-$, a and b are defined above; and

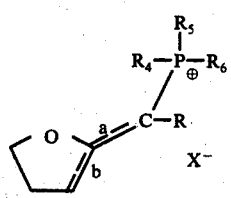

wherein $R_4$, $R_5$ and $R_6$ is each an alkyl radical containing 1-6 carbon atoms, a cycloalkyl radical containing 5 or 6 carbon atoms, an alkylaryl radical wherein alkyl contains 2-4 carbon atoms and aryl may contain substituents of halogen, alkyl containing 1-6 carbon atoms or alkoxy containing 1-6 carbon atoms, or a substituted phenyl radical wherein phenyl has substituents of halogen or alkoxy containing 1-6 carbon atoms; and R, $X^-$, a and b are defined above.

The alkyl radicals containing 1-6 carbon atoms are exemplified by methyl, ethyl, propyl, butyl, pentyl, hexyl and the corresponding branched-chain isomers.

Representative of the alkoxy derivatives containing 1-6 carbon atoms are methoxy, ethoxy, propoxy, butoxy and the branched-chain radicals isomeric therewith.

The cycloalkyl radicals containing 5 or 6 carbon atoms are cyclopentyl and cyclohexyl.

The halo radical denoted by Y are typified by fluoro, chloro, bromo and iodo.

Examples of pharmacologically acceptable anions are chloride, bromide, iodide, acetate, propionate, and benzoate. In addition, non-nucleophylic anions such as tetrafluoroborate and trifluoromethylsulfonate are acceptable when the compounds of this invention are used as intermediates in organic syntheses.

The closest prior art appears to be a thesis by E. T. Shaffer from the University of Delaware, 1967, entitled, "Synthetic Applications of the Wittig Reaction". A compound of the formula

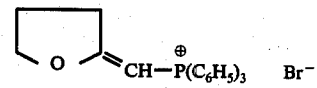

was reasoned to be the end product of a given reaction. The tetrahydrofuran compounds of the present invention differ structurally from the prior art in that the phenyl radicals are substituted with halide or alkoxy substituents, or the phenyl group is attached to an alkyl of from 2 to 4 carbon atoms. The compounds containing the 6 and 7-membered heterocyclic rings are structurally different from the prior art which discloses the compound having a 5-membered heterocyclic ring. Also, no utility was disclosed for the compounds of the prior art while compounds of the present invention are useful as analgesic agents and intermediates in organic synthesis.

DETAILED DESCRIPTION OF THE INVENTION

The compounds of the present invention show analgesic activity but, at the same time, they show activity as morphine antagonists and they would appear to possess a particularly useful combination of the effects.

The analgesic utility of the present compounds is demonstrated by the following test procedure. Groups of 10 male Charles River mice weighing 18-25 g., were treated subcutaneously with vehicle control or test compound. Phenyl-P-benzoquinone (2.5 mg/kg) was administered intraperitoneally 15 minutes later as a 0.025% solution in saline or 5% ethanol. Starting 5 minutes after the phenyl-p-benzoquinone challenge, each mouse was observed for 10 minutes and the number of writhes were counted. A writhe was taken to consist of a combination or sequence or arching of the back, pelvic rotation and hind-limb extension. To achieve maximum sensity, significant analgesia was assumed when an animal's writhing frequency was 50% or less of the control group mean for the day. Estimates of the $ED_{50}$ and slope were determined and estimates of potency compared to morphine were derived. The $ED_{50}$ was defined as the dose which decreased writhing by 50% or more of the control group mean in 50% of the test animals. When tested by the above procedure, [(2-oxepanylidene)methyl]triphenylphosphonium bromide showed an $ED_{50}$ of 3.11 mpk. While other pharmacological effects may be responsible for activity in this test, the present compounds have not been found to be active in tests for these other effects so that the test activity must be associated with an analgesic effect. Morphine antagonism for the present compounds has been demonstrated in the standard hot plate procedure. Ampules of the present compounds containing 100 mg. can be prepared for parenteral administration using standard solutions. The usual dose for a single administration would be 50–300 mg. parenterally.

The present compounds are also useful in organic synthesis. Thus, the preparation of the present phosphonium salts can be used as a method for purifying the phosphoranes or acyclic phosphonium salts from which they are obtained. Regeneration of the phosphorane can be accomplished by treating the present compounds with an acid such as hydrochloric acid to give the corresponding (ω-chloro-2-oxoalkyl)tri(substituted)phosphonium salt, which is then treated with base to give the phosphorane. Also, depending on the acid used to open up the cyclic compound, this can serve as a method for obtaining other substituted phosphoranes which are different from the original compound. The substituted phosphoranes themselves can be reacted with an appropriate aldehyde or ketone by standard procedure to give the corresponding product.

The present compounds are prepared from phosphoranes of the formulas

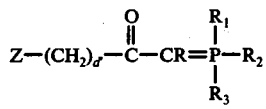

and

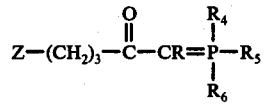

wherein Z is preferably a halogen such as chlorine or bromine, $d'$ is 4 or 5, and R, $R_1$, $R_2$, $R_3$, $R_4$, $R_5$ and $R_6$ are defined above. The reaction is carried out with heating in an inert solvent. Preferred solvents are aromatic hydrocarbons such as benzene or toluene. The anion of the salt obtained would correspond to Z but salts involving other anions can be obtained readily by ion exchange procedures or by mixing an aqueous solution of the phosphonium salt with a mineral salt.

The products obtained by the above procedure are mixed isomers of formula 1, 2 or 3, depending upon the starting material used. For example, when $d'$ is 5 in the starting material, the products obtained are

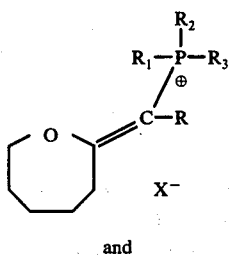

and

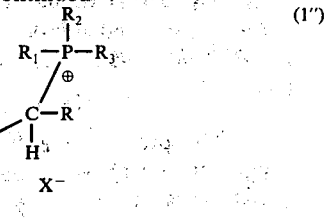

Similar mixed isomers of the pyran and furan compounds are obtained when $d'$ is 4 or 3. The isomers can be readily separated by chromatography.

The (ω-haloalkanoylmethylene)tri(substituted) phosphorane starting materials are obtained by processes originating with hydroxyalkanoic acid lactones of the following formula

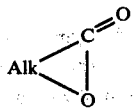

wherein Alk represents an alkylene of 3, 4 or 5 carbon atoms. These lactones and methods for their preparation are described by Starcher and Phillips, [J. Am. Chem. Soc., 80, 4079 (1958)] and by House, ["Modern Synthetic Reactions", p. 323, 2nd edition, W. A. Benjamin, Inc., Menlo Park, Calif. (1972)]. These lactones are converted to the corresponding ω-haloalkanoyl halides, typically by the method described by Reppe et al., [Ann., 596, 158 (1955)]for the synthesis of 4-chlorobutyryl chloride from γ-butyrolactone. Reaction of the ω-haloalkanoyl halides with diazoalkane affords the corresponding diazoketones, which when treated with hydrochloric, hydrobromic or hydroiodic acid, yield the ω-haloalkylhaloalkyl ketones. The latter substances ae allowed to react with trisubstituted phosphines to produce the corresponding (ω-halooxoalkyl)-tri-(substituted)Phosphonium chlorides, which are converted to the corresponding (ω-haloalkanoylmethylene)tri-(substituted)phosphoranes by reaction with a base, such as an alkaline metal hydroxide or carbonate.

The latter reactions are exemplified by the cleavage of δ-valerolactone with zinc chloride and thionyl chloride to produce 5-chlorovaleryl chloride, reaction of that acid chloride with diazomethane, followed by treatment of the resulting diazomethylketone with hydrochloric acid to yield 1,6-dichloro-2-hexanone, and reaction of that ketone with triphenylphosphine to afford (6-chloro-2-oxohexyl) triphenylphosphonium chloride. This product is converted to (5-chloropentanoylmethylene)triphenyl phosphorane by reaction with aqueous sodium hydroxide.

An alternate method for manufacture of the (ω-haloalkanoylmethylene)tri-(substituted)phosphoranes, wherein the halo substituent is other than chloro, involves heating (ω-chloroalkanoylmethylene)tri-(substituted) phosphoranes in a suitable solvent such as benzene to afford the corresponding heterocyclic phosphonium chloride, reacting that heterocyclic phosphonium salt with the appropriate alkali metal halide, e.g., sodium bromide, sodium iodide, etc., then reacting the resulting heterocyclic phosphonium halide with the corresponding hydrohalic acid, resulting in cleavage of the ring to yield the desired phosphonium salt. As a specific example, (5-chloropentanoylmethylene)-triphenylphosphorane is heated in benzene to afford [(tetrahydro-2H-pyran-2-ylidene)methyl]triphenyl phosphonium chloride which has the following structure

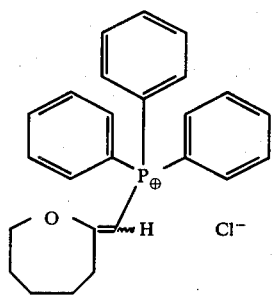

This compound is then contacted with sodium bromide to afford the corresponding phosphonium bromide, and the latter salt is heated with hydrobromic acid to yield (6-bromo-2-oxohexyl)triphenylphosphonium bromide. Reaction of that salt with aqueous sodium hydroxide affords (5-bromo-pentanoylmethylene)triphenyl phosphorane.

The invention will appear more fully from the examples which follow. These examples are not to be construed as limiting the invention either in spirit or in scope as many modifications, both in materials and methods, will be apparent to those skilled in the art. In these examples, temperatures are given in degrees Centigrade (°C.) and quantities of materials in parts by weight except as otherwise noted. Nuclear magnetic resonance peaks are given in cps (cycles per second) downfield from an internal standard TMS (tetramethylsilane). Decomposition of the phosphonium salts occur at the indicated melting points.

EXAMPLE 1

To an ethereal solution of diazomethane (prepared by the reaction of 90 parts of N-nitrosomethylurea with 175 parts by volume of 45% aqueous potassium hydroxide in 375 parts by volume of ether) is added dropwise, at 0° C., 50 parts of 5-chlorovaleryl chloride and the resulting reaction mixture is alowed to warm to room temperature with stirring, then stirred for an additional 16 hours. A saturated solution of dry hydrogen chloride in ether is then added portionwise to the point at which the solution becomes colorless. This solution containing the diazoketone and hydrogen chloride is stirred at room temperature for about 16 hours, then is washed successively with water, saturated aqueous sodium chloride and dried over anhydrous sodium sulfate. Removal of the solvent by distillation under reduced pressure affords 1,6-dichloro-2-hexanone.

To a solution of 41 parts of 1,6-dichloro-2-hexanone in 400 parts by volume of benzene is added 44 parts of triphenylphosphine and the resulting solution is stored, in the absence of light for about 6 days, at the end of which time the crude product has crystallized from the mixture. That material is collected by filtration and is purified by recrystallization from acetone to afford (6-chloro-2-oxohexyl)triphenylphosphonium chloride. This product melts at 158°–161° C. and is characterized by 60-MHz nuclear magnetic resonance peaks in CDCl$_3$ (deuterated chloroform) at 100 cps (multiplet), 140 cps (multiplet), 180 cps (multiplet), 208 cps (multiplet) and 357 cps (doublet, J$\simeq$12) in addition to the aromatic protons. The C$_1$ protons at 375 cps exchange with D$_2$O (deuterated water).

A solution of 20 parts of (6-chloro-2-oxo-hexyl)-triphenylphosphonium chloride in 200 parts of water is made alkaline by the addition of a 50% aqueous sodium hydroxide solution and extracted with benzene. The combined organic extracts are dried over anhydrous sodium sulfate, then stripped of solvent under reduced pressure to afford (5-chloropentanoylmethylene) triphenylphosphorane.

A solution containing 20 parts of (5-chloropentanoylmethylene)triphenylphosphorane in 200 parts of benzene is heated at the reflux temperature for about 16 hours. Evaporation of the solvent affords a product which is a mixture of [(tetrahydro-2H-pyran-2-ylidene)methyl]triphenyl-phosphonium chloride and [(5,6-dihydropyran-2-yl)methyl]-triphenylphosphonium chloride.

The mixture is separated by low pressure liquid chromatography. A column packed with Merck Silica 60, 230–400 mesh, is equilibrated with 500 parts of 95% ethanol-5% water and then 2000 parts ethyl acetate. 1 part of the product is combined with 1000 parts eluent consisting of approximately 25% ethanol, 2% water and 73% benzene, and is passed through the column. The flow rate is maintained by a Milroyal D pump.

The first of the two desired compounds eluted is [(5,6-dihydrofuran-2-yl)methyl]triphenylphosphonium chloride. This product is characterized by 60 MHz nuclear magnetic resonance peaks in CDCl$_3$ at 108 cps (multiplet), 162 cps (triplet), 246 cps (triplet), 246 cps (doublet, J$\simeq$13 cps), 294 cps (multiplet), and 462 cps (multiplet) and is represented by the following structure

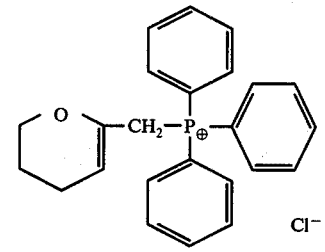

The second compound, [(tetrahydro-2H-pyran-2-ylidene)methyl]triphenylphosphonium chloride, is characterized by 60 MHz nuclear magnetic resonance peaks in CDCl$_3$ at about 107 cps (multiplet), 170 cps (multiplet), 228 cps (multiplet) and 329 cps (doublet, J$\simeq$18 cps) in addition to the aromatic protons. This compound melted at about 215°– 221° C. and is represented by the following structure

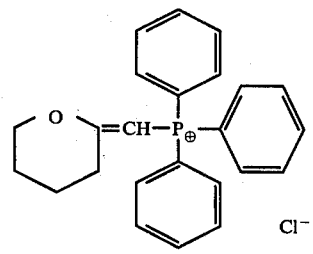

EXAMPLE 2

A solution consisting of 18.5 parts of [(tetrahydro-2H-pyran-2-ylidene)methyl]triphenylphosphonium chloride in 100 parts by volume of concentrated hydrochloric acid is heated at the reflux temperature for about 36 hours, then is cooled to room temperature. The solvent is removed by distillation under reduced pressure to afford (6-chloro-2-oxohexyl)triphenylphosphonium chloride, identical with the product of paragraph 2 of Example 1.

EXAMPLE 3

A solution consisting of 2.1 parts of [(tetrahydro-2H-pyran-2-ylidene)methyl]triphenylphosphonium chloride in 50 parts of water is added with stirring to 2 parts of sodium bromide. At the end of about 5 minutes an additional 4 parts of sodium bromide is added and the mixture is stirred until precipitation is complete. The precipitate is isolated by filtration, thus affording [(tetrahydro-2H-pyran-2-ylidene)methyl]triphenylphosphonium bromide. This product melts at 205°–209° C. and is characterized by 60 MHz nuclear magnetic resonance peaks in CDCl$_3$ (deuterated chloroform) at 107 cps (multiplet), 170 cps (multiplet), 228 cps (multiplet), 329 cps (doublet, J≃18 cps) in addition to the aromatic protons, and by microanalytic determination of bromide.

EXAMPLE 4

A solution of 68 parts of imidazole in 225 parts of tetrahydrofuran is cooled to 5° C. and a solution of 99.3 parts of 5-bromovaleryl chloride in 175 parts of ether is added slowly over 30 minutes with stirring. The mixture is then stirred an additional 30 minutes at room temperature before it is filtered quickly to remove the imidazole hydrochloride. The resulting filter cake is washed with ether and the combined filtrate which is a solution of 1-(5-bromopentanoyl)imidazole, is kept under nitrogen.

To a slurry of 180 parts of methyltriphenyl-phosphonium bromide in 280 parts of ether is added 500 parts by volume of an ether-hexane solution containing 42 parts of phenyllithium at room temperature with stirring under nitrogen. The resulting mixture is stirred for one hour under nitrogen and then cooled to −70° C. and the amide solution prepared in the preceding paragraph is added slowly over a period of 30 minutes. Stirring is continued at −70° C. for 30 minutes and the mixture is allowed to warm up to 10° C. over 30 minutes before it is poured in 5000 parts by volume of 1M hydrochloric acid. The aqueous layer is separated and made alkaline with potassium carbonate. An oil forms and this is extracted well with toluene. The toluene solution is filtered through infusorial earth and concentrated to a volume of 500 parts to provide a toluene solution of (5-bromo-pentanoylmethylene)triphenylphosphorane.

The toluene solution of (5-bromopentanoylmethylene)triphenylphosphorane obtained in the preceding paragraph is heated at reflux for 16 hours with stirring. Evaporation of the solvent affords a product which is a mixture of [(tetrahydro-2H-pyran-2-ylidene)methyl]triphenyl phosphonium bromide and [(5,6-dihydropyran-2-yl)-methyl]triphenylphosphonium bromide which are separated by low pressure liquid chromatography.

EXAMPLE 5

A solution consisting of 1.6 parts of [(tetrahydro-2H-pyran-2-ylidene)methyl]triphenylphosphonium bromide in 25 parts by volume of 48% hydrobromic acid was heated at the reflux temperature for about 5 hours, then was stripped of solvent under reduced pressure affording the crude product as an amber colored oil. Trituration of that oily material with benzene, followed by evaporation of the benzene under an atmosphere of nitrogen afforded (6-bromo-2-oxohexyl)triphenylphosphonium bromide. This product exhibited 60 MHz nuclear magnetic resonance peaks in CDCl$_3$ (deuterated chloroform) at about 100 cps (multiplet), 180 cps (multiplet), 200 cps (multiplet), 357 cps (doublet, J≃cps) in addition to the aromatic protons.

EXAMPLE 6

When an equivalent quantity of tri(p-methoxyphenyl)-phosphine is substituted for the triphenylphosphine in Example 1, and the procedure detailed therein is substantially repeated, there is obtained [(5,6-dihydropyran-2-yl)methyl]tri(p-methoxyphenyl)phosphonium chloride which is characterized by 60 MHz nuclear magnetic resonance peaks in CDCl$_3$ at 108 cps (multiplet), 221 cps (triplet), 237 cps (singlet), 257 (doublet, J≃13 cps) and 438 cps (multiplet) and is represented by the structure

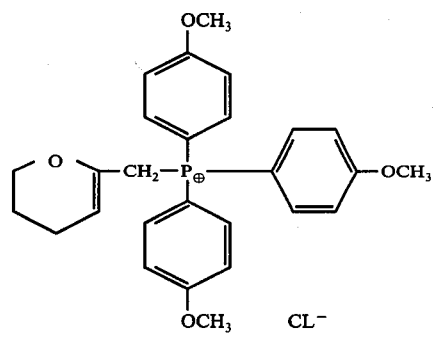

and [(tetrahydro-2H-pyran-2-ylidene)methyl]tri(p-methoxy-phenyl)phosphonium chloride which is characterized by 60 MHz nuclear magnetic resonance peaks in CDCl$_3$ at 111 cps (multiplet), 172 cps (triplet), 232 cps (multiplet), 256 cps (singlet), 444 cps (multiplet), and 329 cps (doublet, J≃17 cps) and is represented by the structure

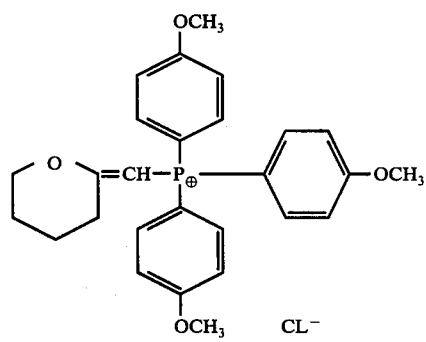

EXAMPLE 7

When an equivalent quantity of tri(p-methylphenyl)-phosphine is substituted for the triphenylphosphine in Example 1, and the procedure detailed therein is substantially repeated, there is obtained [(5,6-dihydropyran-2-yl)-methyl]tri(p-methylphenyl)phosphonium chloride which is represented by the structure

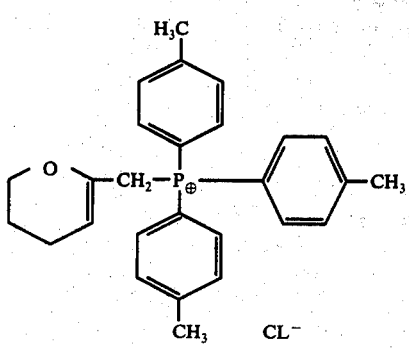

and [(tetrahydro-2H-pyran-2-ylidene)methyl]tri(p-methylphenyl)phosphonium chloride which melts at 210°–212° C. and is represented by the structure

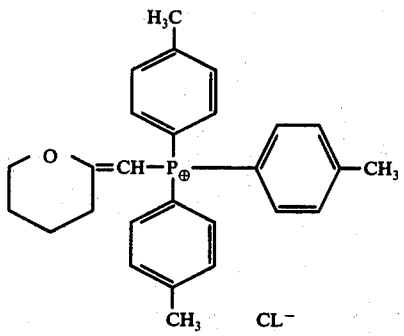

EXAMPLE 8

When an equivalent quantity of methyl(diphenyl)-phosphine is substituted for the triphenylphosphine in Example 1, and the procedure detailed therein is substantially repeated, there is obtained [(5,6-dihydropyran-2-yl)-methyl]methyl(diphenyl) phosphonium chloride which is represented by the structure

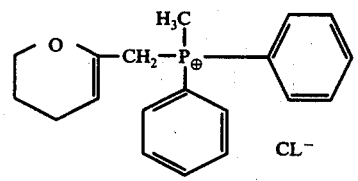

and [(tetrahydro-2H-pyran-2-ylidene)methyl]methyl(-diphenyl)-phosphonium chloride which is represented by the structure

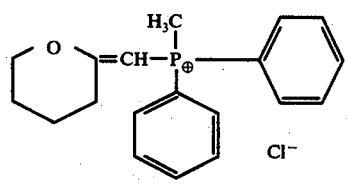

EXAMPLE 9 when an equivalent quantity of triethylphosphine is substituted for the triphenylphosphine in Example 1, and the procedure detailed therein is substantially repeated, there is obtained [(5,6-dihydropyran-2-yl)methyl]triethylphosphonium chloride which is very hydrophilic having a melting range of 100° – 125° C, and is represented by the structure

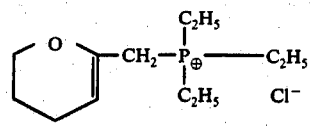

and [(tetrahydro-2H-pyran-2-ylidene)methyl]triethylphosphonium chloride which is represented by the structure

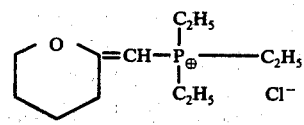

EXAMPLE 10

When an equivalent quantity of tri(p-fluorophenyl)-phosphine is substituted for the triphenylphosphine in Example 1, and the procedure detailed therein is substantially repeated, there is obtained [(5,6-dihydropyran-2 -yl)methyl]tri(p-fluorophenyl)phosphonium chloride which is represented by the structure

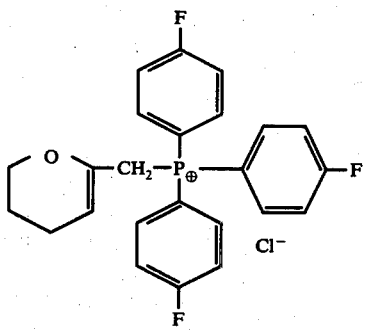

and [(tetrahydro-2H-pyran-2-ylidene)methyl]tri(p-fluorophenyl)phosphonium chloride which melts at 199° – 202° C. and is represented by the structure

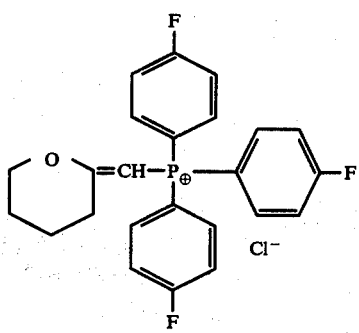

EXAMPLE 11

When an equivalent quantity of ethyltriphenyl-phosphonium chloride is substituted for the methyltriphenylphosphonium bromide in Example 2, and the procedure detailed therein is substantially repeated, there is obtained [(5,6-dihydropyran-2-yl)ethyl]triphenylphosphonium chloride which is characterized by 100 MHz nuclear magnetic resonance peaks in CDCl$_3$ at 740 cps (multiplet), 540 cps (multiplet), two multiplets symmetrical about 362 cps, and four singlets arising above the methylene envelope symmetrical about 163 cps (J≃7 cps and J≃structure 19 cps) and is represented by the

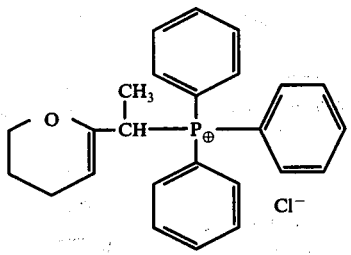

and [1-(tetrahydro-2H-pyran-2-ylidene)ethyl]triphenylphosphonium chloride which is represented by the structure

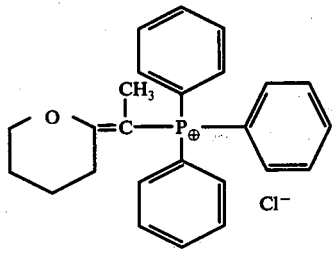

EXAMPLE 12

When an equivalent quantity of 6-chlorohexanoyl chloride is subjected to the successive processes described in Example 1 there is obtained [(4,5,6,7-tetrahydrooxepin-2-yl)methyl]triphenylphosphonium chloride which is characterized by 60 MHz nuclear magnetic resonance peaks in CDCl₃ at 213 cps (triplet), 243 cps (doublet, J≃13 cps), 288 cps (multiplet), and 446 cps (multiplet) and is represented by the structure

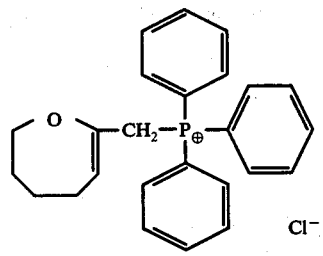

and [(2-oxepanylidene)methyl]triphenylphosphonium chloride which is represented by the structure

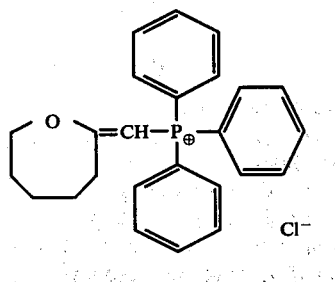

Substitution of an equivalent quantity of [(2-oxepanylidene)methyl]triphenylphosphonium chloride in the procedure of Example 3 resulted in [(2-oxepanylidene)-methyl]triphenylphosphonium bromide, melting at about 223° - 226° C.

EXAMPLE 13

When equivalent quantities of 4-chlorobutanoyl chloride and tri(p-fluorophenyl)phosphine are substituted for the 5-chloropentanoyl chloride and triphenylphosphine in Example 1, and the procedure detailed therein is substantially repeated, there is obtained [(4,5-dihydrofuran-2-yl)methyl]tri(p-fluorophenyl)phosphonium chloride which is characterized by 60 MHz nuclear magnetic resonance peaks in CDCl₃ at 211 cps (doublet, J≃13 cps), 309 cps (multiplet) and 456 cps (multiplet) and is represented by the structure

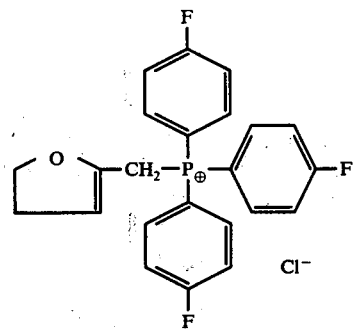

and [(tetrahydro-2H-furan-2-ylidene)methyl]tri(p-fluorophenyl)phosphonium chloride which is characterized by 60 MHz nuclear magnetic resonance peaks in CDCl₃ at 136 cps (multiplet), 202 cps (multiplet), 262 cps (triplet), 359 cps (doublet, J≃16 cps), and 456 cps (multiplet) and is represented by the structure

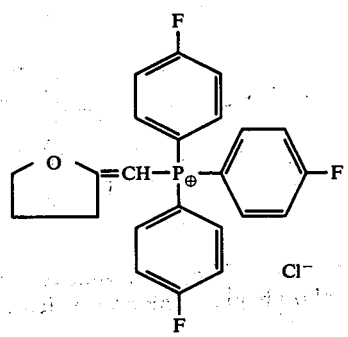

What we claim is:
1. A compound of the formula

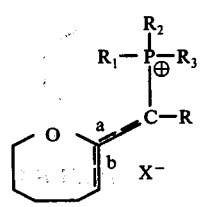

wherein R is hydrogen or an alkyl containing 1-3 carbon atoms, $R_1$, $R_2$ and $R_3$ is each an alkyl radical containing 1-6 carbon atoms, a cycloalkyl radical containing 5 or 6 carbon atoms, or a radical of the formula

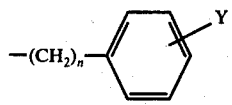

wherein n is 0–4, and Y is hydrogen, halogen, alkyl containing 1–6 carbon atoms or alkoxy containing 1–6 carbon atoms; X⁻ is a pharmacologically acceptable anion; and one of a and b is a double bond and the other is a single bond.

2. A compound according to claim 1 of the formula

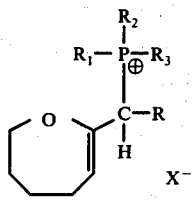

wherein R is hydrogen or an alkyl containing 1–3 carbon atoms, R₁, R₂ and R₃ is each an alkyl radical containing 1–6 carbon atoms, a cycloalkyl radical containing 5 or 6 carbon atoms, or a radical of the formula

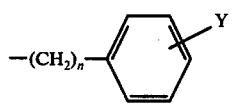

wherein n is 0–4, and Y is hydrogen, halogen, alkyl containing 1–6 carbon atoms or alkoxy containing 1–6 carbon atoms; and X⁻ is a pharmacologically acceptable anion.

3. A compound according to claim 1 of the formula

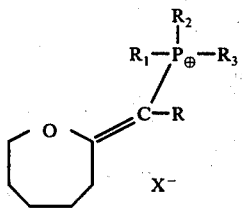

wherein R is hydrogen or an alkyl containing 1–3 carbon atoms, R₁, R₂ and R₃ is each an alkyl radical containing 1–6 carbon atoms, a cycloalkyl radical containing 5 or 6 carbon atoms, or a radical of the formula

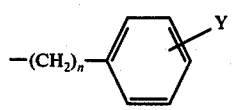

wherein n is 0–4, and Y is hydrogen, halogen, alkyl containing 1–6 carbon atoms or alkoxy containing 1–6 carbon atoms; and X⁻ is a pharmacologically acceptable anion.

4. As in claim 1, the compound which is [(2-oxepanylidene)methyl]triphenylphosphonium chloride.

5. As in claim 1, the compound which is [(4,5,6,7-tetrahydrooxepin-2-yl)methyl]triphenylphosphonium chloride.

6. As in claim 1, the compound which is [(2-oxepanylidene)methyl]triphenylphosphonium bromide.

7. A compound of the formula

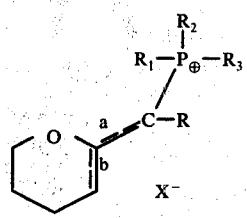

wherein R is hydrogen or an alkyl containing 1–3 carbon atoms, R₁, R₂ and R₃ is each an alkyl radical containing 1–6 carbon atoms, a cycloalkyl radical containing 5 or 6 carbon atoms, or a radical of the formula

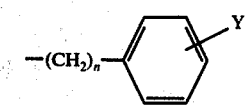

wherein n is 0–4, and Y is hydrogen, halogen, alkyl containing 1–6 carbon atoms or alkoxy containing 1–6 carbon atoms; X⁻ is a pharmacologically acceptable anion; and one of a and b is a double bond and the other is a single bond.

8. A compound according to claim 7 of the formula

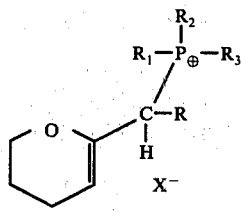

wherein R is hydrogen or an alkyl containing 1–3 carbon atoms, R₁, R₂ and R₃ is each an alkyl radical containing 1–6 carbon atoms, a cycloalkyl radical containing 5 or 6 carbon atoms, or a radical of the formula

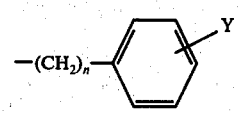

wherein n is 0–4, and Y is hydrogen, halogen, alkyl containing 1–6 carbon atoms or alkoxy containing 1–6 carbon atoms; and X⁻ is a pharmacologicaly acceptable anion.

9. A compound according to claim 7 of the formula

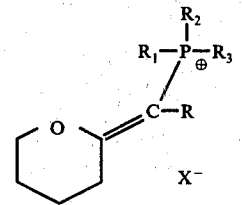

wherein R is hydrogen or an alkyl containing 1–3 carbon atoms, R₁, R₂ and R₃ is each an alkyl radical containing 1–6 carbon atoms, a cycloalkyl radical containing 5 or 6 carbon atoms, or a radical of the formula

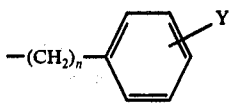

wherein n is 0-4, and Y is hydrogen, halogen, alkyl containing 1-6 carbon atoms or alkoxy containing 1-6 carbon atoms; and X⁻ is a pharmacologically acceptable anion.

10. As in claim 7, the compound which is [(tetrahydro-2H-pyran-2-ylidene)methyl]triphenylphosphonium chloride.

11. As in claim 7, the compound which is [(tetrahydro-2H-pyran-2-ylidene)methyl]methyl(diphenyl)phosphonium chloride.

12. As in claim 7, the compound which is [(5,6-dihydropyran-2-yl)methyl]triethylphosphonium chloride.

13. As in claim 7, the compound which is [(tetrahydro-2-H-pyran-2-ylidene)methyl]tri(p-methoxyphenyl)-phosphonium chloride.

14. As in claim 7, the compound which is [(5,6-dihydropyran-2-yl)methyl]tri(p-methoxyphenyl)phosphonium chloride.

15. As in claim 7, the compound which is [1-(tetrahydro-2-H-pyran-2-ylidene)ethyl]triphenylphosphonium chloride.

16. A compound of the formula

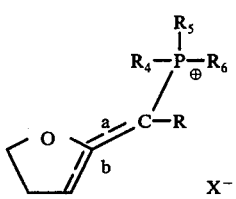

wherein R is hydrogen or an alkyl containing 1-3 carbon atoms, $R_4$, $R_5$, and $R_6$ is each an alkyl radical containing 1-6 carbon atoms, a cycloalkyl radical containing 5 or 6 carbon atoms, an alkylaryl radical wherein alkyl contains 2-4 carbon atoms and aryl may contain substituents of halogen, alkyl containing 1-6 carbon atoms or alkoxy containing 1-6 carbon atoms, or a substituted phenyl radical wherein phenyl has substituents of halogen or alkoxy containing 1-6 carbon atoms; X⁻ is a pharmacologically acceptable anion; and one of a and b is a double bond and the other is a single bond.

17. A compound according to claim 16 of the formula

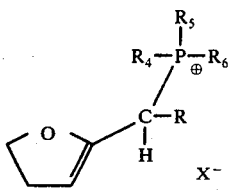

wherein R is hydrogen or alkyl containing 1-3 carbon atoms, $R_4$, $R_5$, and $R_6$ is each an alkyl radical containing 1-6 carbon atoms, a cycloalkyl radical containing 5 or 6 carbon atoms, an alkyl aryl radical wherein alkyl contains 2-4 carbon atoms and aryl may contain substituents of halogen, alkyl containing 1-6 carbon atoms or alkoxy containing 1-6 carbon atoms, or a substituted phenyl radical wherein phenyl has substituents of halogen or alkoxy containing 1-6 carbon atoms; and X⁻ is a pharmacologically acceptable anion.

18. A compound according to claim 16 of the formula

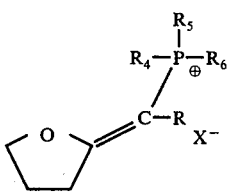

wherein R is hydrogen or an alkyl containing 1-3 carbon atoms, $R_4$, $R_5$, and $R_6$ is each an alkyl radical containing 1-6 carbon atoms, a cycloalkyl radical containing 5 or 6 carbon atoms, an alkylaryl radical wherein alkyl contains 2-4 carbon atoms and aryl may contain substituents of halogen, alkyl containing 1-6 carbon atoms or alkoxy containing 1-6 carbon atoms, or a substituted phenyl radical wherein phenyl has substituents of halogen or alkoxy containing 1-6 carbon atoms; and X⁻ is a pharmacologically acceptable anion.

19. As in claim 16, the compound which is [(tetrahydro-2H-furan-2-ylidene)methyl]tri(p-fluorophenyl)-phosphonium chloride.

20. As in claim 16, the compound which is [(4,5-dihydrofuran-2-yl)methyl]tri(p-fluorophenyl)phosphonium chloride.

* * * * *